United States Patent [19]

Castro

[11] Patent Number: 5,393,526
[45] Date of Patent: Feb. 28, 1995

[54] COSMETIC COMPOSITIONS

[75] Inventor: John R. Castro, Stamford, Conn.

[73] Assignee: Elizabeth Arden Company, Division of Conopco, Inc., New York, N.Y.

[21] Appl. No.: 192,928

[22] Filed: Feb. 7, 1994

[51] Int. Cl.$^6$ .................... A61K 7/00; A61K 35/78
[52] U.S. Cl. .................... 424/195.1; 424/401; 514/557; 514/847
[58] Field of Search .................... 424/195.1, 74, 401

[56] References Cited

U.S. PATENT DOCUMENTS

| | | | |
|---|---|---|---|
| 4,105,782 | 8/1978 | Yu et al. | 424/283 |
| 4,105,783 | 8/1978 | Yu et al. | 424/283 |
| 4,197,316 | 4/1980 | Yu et al. | 424/317 |
| 4,234,599 | 11/1980 | Van Scott et al. | 424/279 |
| 4,354,035 | 10/1982 | Christ | 560/75 |
| 4,424,234 | 1/1984 | Alderson et al. | 424/317 |
| 4,795,638 | 1/1989 | Ayache | 424/195.1 |
| 4,880,621 | 11/1989 | Grollier | 424/63 |
| 4,942,033 | 7/1990 | Aubert | 424/195.1 |
| 5,091,171 | 2/1992 | Yu et al. | 424/642 |

Primary Examiner—Thurman K. Page
Assistant Examiner—Sally Gardner
Attorney, Agent, or Firm—Milton L. Honig

[57] ABSTRACT

Cosmetic compositions, especially color cosmetics such as facial foundations, are described that include $C_2-C_{28}$ α-hydroxy carboxylic acid, rosmarrinic acid as well as salts of the foregoing in pharmaceutically acceptable carriers. These compositions are effective against the signs of aging such as fine lines and wrinkles while being non-irritating to the skin.

8 Claims, No Drawings

COSMETIC COMPOSITIONS

BACKGROUND OF THE INVENTION

1. Field of the Invention

The invention concerns cosmetic compositions, especially color cosmetics such as facial foundations, effective at counteracting the signs of aging including fine lines and wrinkles while remaining non-irritating to the treated skin.

2. The Related Art

Emollients such as fats, phospholipids and sterols have in the past been used to soften wrinkled or dry skin. These emollients are only partially effective as a remedy for skin in poor condition.

The use of α-hydroxy carboxylic acids for enhancing the quality of human skin has been known for some time. There is no doubt that α-hydroxy carboxylic acids are therapeutically effective much beyond the common emollients.

U.S. Pat. No. 4,424,234 (Alderson et al.) discloses skin treatment compositions incorporating α-hydroxycaproic acid and α-hydroxycaprylic acid or mixtures thereof in compositions that have a pH value of less than 7, usually from 2 to 4. Yu and Van Scott have patented widely in this area. For instance, U.S. Pat. No. 4,105,782 reports amines or ammonium salts of α-hydroxy carboxylic acids in the treatment of acne or dandruff. In U.S. Pat. No. 4,105,783 and U.S. Pat. No. 4,197,316, these compounds are suggested for the treatment of dry skin. U.S. Pat. No. 4,234,599 discloses the use of α-hydroxy carboxylic acids, their esters or amine salts in the treatment of keratoses. More recently, U.S. Pat. No. 5,091,171 focused attention on these compounds as being effective against age spots, wrinkles and aging related skin changes.

While α-hydroxy carboxylic acids hold much therapeutic promise, these materials have been found to irritate human skin on repeated topical applications. The irritation may range from a sensation of tingling, itching and burning to clinical signs of redness and peeling. Causes for such irritation have been linked to the lowering of pH in the stratum corneum of human skin. Low pH has been suggested as provoking disturbances in intercorneocyte bondings resulting in adverse skin reactions, specially in some individuals with sensitive skin.

Accordingly, it is an object of the present invention to provide a composition including α-hydroxy carboxylic acids with a carrier formulation that avoids irritation including the sensation of stinging, itching and burning as well as any clinical signs of redness and peeling.

It is another object of the present invention to provide a cosmetic composition that is functionally effective against age spots, wrinkling and related aging changes.

Still another object of the present invention is to provide a cosmetic composition, especially a color cosmetic such as a facial foundation, which exhibits a smooth silky, slippery texture.

These and other objects of the present invention will become more readily apparent from consideration of the following summary, detailed description and examples which follow.

SUMMARY OF THE INVENTION

A cosmetic composition is provided that includes:

(i) from about 0.01 to about 15% by weight of a $C_2$–$C_{28}$ α-hydroxy carboxylate compound;

(ii) from about 0.001 to about 10% by weight of rosmarrinic acid or salt thereof; and (iii) from about 1 to about 99.9% by weight of a pharmaceutically acceptable carrier.

DETAILED DESCRIPTION

Irritation and stinging attributed to $C_2$–$C_{28}$ α-hydroxy carboxylates have now been found to be considerably reduced through formulation with rosmarrinic acid or salts thereof.

Accordingly, the first critical component of compositions according to the present invention is a $C_2$–$C_{28}$ α-hydroxy carboxylate compound, the term "compound" being defined as including acid and salt forms as well as mixtures thereof.

A wide variety of α-hydroxy carboxylate compounds may be employed for purposes of the present invention. Suitable acid examples include:

α-hydroxyethanoic acid
α-hydroxypropanoic acid
α-hydroxyhexanoic acid
α-hydroxyoctanoic acid
α-hydroxydecanoic acid
α-hydroxydodecanoic acid
α-hydroxytetradecanoic acid
α-hydroxyhexadecanoic acid
α-hydroxyoctadecanoic acid
α-hydroxyeicosanoic acid
α-hydroxydocosanoic acid
α-hydroxyhexacosanoic acid, and
α-hydroxyoctacosanoic acid Particularly preferred from the above list are α-hydroxyethanoic acid (commonly known as glycolic acid), α-hydroxypropanoic acid (commonly known as lactic acid) and α-hydroxyoctanoic acid (commonly known as α-hydroxycaprylic acid or HCA).

Levels of α-hydroxy carboxylate compounds may range from about 0.01 to about 15%, preferably between about 0.2 and 10%, optimally between about 0.5 and 5% by weight.

A second critical component of compositions according to the present invention is that of rosmarrinic acid, salts thereof and any mixtures of acid and salt derivatives. A major natural source of rosmarrinic acid is sage extract. When in salt form, the counterion to rosmarrinate may be an alkalimetal, ammonium or $C_1$–$C_{20}$ alkyl or alkanol ammonium cation. Levels of rosmarrinic acid or salt may range from about 0.001 to about 10%, preferably from about 0.05 to about 5%, optimally from about 0.3 to about 1% by weight.

Cosmetic compositions in the form of color cosmetics generally require one or more pigments. Titanium dioxide is the most common pigment normally present in such products. Particularly preferred is micronized titanium dioxide having an average particle size of less than 100 nm, preferably between 0.1 and 40 nm, optimally between 1 and 10 nm. Oil-dispersible titanium dioxide is especially useful. This variety has hydrophobic surface properties resulting from coating with organic esters, metal soaps (e.g. aluminum stearate) or organo silicone compounds. Most preferred is a micronized titanium dioxide coated with dimethicone and suspended in caprylic/capric triglyceride available under the trademark Tioveil G (40% active) sold by the Tioxide Company. Amounts of titanium dioxide may range from about 0.1 to about 20%, preferably from about 0.5 to about 10%, optimally from about 2 to about 4% by weight.

Another category of pigments normally present in color cosmetics is that of iron oxides. These pigments will also preferably have hydrophobic surface properties imparted by a coating such as an ester or organo silicone substance. Preferred pigments are hydrophobic yellow iron oxide, hydrophobic red iron oxide and hydrophobic black iron oxide. Amounts of the iron oxide may range anywhere from about 0.01 to about 20%, preferably from about 0.2 to about 10%, optimally from about 1 to about 5% by weight.

Talc may also be incorporated into cosmetic compositions of the present invention. Most preferred are talcs of hydrophobic surface properties imparted by an ester or organo silicone coating (e.g. methicone). Amounts of the talc may range from 0.01 to about 80%, preferably from about 0.1 to about 10%, optimally from about 0.2 to about 5% by weight.

Cosmetic compositions of the present invention may be aqueous or anhydrous formulations. They may also be in any form such as liquids, gels, creams, lotions and powders.

When compositions of the present invention are formulated as liquids such as facial foundations, they will usually be oil and water emulsions, especially those where the continuous phase is water. Amounts of water that may be present can range from about 5 to about 90%, preferably from about 30 to about 55%, optimally between about 35 and 45% by weight.

Monohydric and polyhydric alcohols may also be present in the aqueous phase. Examples include monohydric $C_1$–$C_3$ alkanols such as ethanol and isopropanol. Polyhydric $C_2$–$C_{10}$ alkanols that may be useful include propylene glycol, butylene glycol, polyethylene glycol and polypropylene glycol. Amounts of the alkanols may range from about 1 to about 50%, preferably from about 5 to about 30%, optimally between about 5 to about 15% by weight of the total composition.

Emollient materials in the form of silicone oils and synthetic esters may be utilized to constitute the oil phase. Amounts of the emollients may range anywhere from about 0.1 to about 70%. preferably from about 1 to about 40%, optimally from about 10 to about 30% by weight of the total composition.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Examples of preferred volatile silicone oils useful herein include: Dow Corning 344, Dow Corning 345 and Dow Corning 200 (manufactured by Dow Corning Corp.).

The nonvolatile silicone oils useful in compositions of this invention are exemplified by the polyalkyl siloxanes, polyalkylaryl siloxanes and polyether siloxane copolymers. The essentially nonvolatile polyalkyl siloxanes useful herein include, for example, polydimethyl siloxanes with viscosities of from about 5 to about 100,000 centistokes at 25° C.

Among the preferred silicones is a material marketed by the Dow Corning Corporation as DC 3225C® which is a cyclomethicone-dimethicone copolyol silicone fluid having a viscosity at 25° C. of 600–2000 cps and a specific gravity of about 0.963. Another preferred silicone is Dow Corning Q2-1403 fluid with components identified by the CTFA names of Dimethicone and Dimethiconol (12–14%) mixture having a viscosity at 25° C. of about 4000 cs and a specific gravity of 0.98.

Among the preferred nonvolatile silicone oils is a Dow Corning product sold under the trademark Cosmetic Wax 2501 which is a dimethicone copolyol of melting point range 28° to 34° C.

Silicones may be present in amounts ranging from about 0.1 up to about 60%, preferably from about 2 to about 25%, optimally between about 10 and 20% by weight.

Among the ester emollients are:

(1) Alkenyl esters of fatty acids having 10 to 20 carbon atoms. Examples thereof include oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyi stearate.

(5) Sterols esters, of which cholesterol fatty acid esters are examples thereof.

Fatty alcohols and fatty acids having from 10 to 20 carbon atoms may also be included as emollients in compositions of the present invention. Especially preferred are such compounds as cetyl, myristyl, palmityl, isostearyl and stearyl alcohols and acids.

Emulsifiers may also be incorporated into cosmetic compositions of the present invention. These emulsifiers may range from 0.5 to 30%, preferably from 1 to 15%, optimally from 3 to 8% by weight. Emulsifiers may be nonionic, anionic, cationic or amphoteric in nature.

Another category of functional ingredient within the cosmetic compositions of the present invention are thickeners. A thickener will usually be present in amounts anywhere from 0.1 to 20% by weight, preferably from about 0.5 to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums and waxes in excess of 10 centistokes and esters such as glycerol stearate have dual functionality.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds.

Particularly preferred preservatives are methyl paraben, propyl paraben, imidazolidinyl urea, sodium dehydroxyacetate and benzyl alcohol. Preservatives will usually be employed in amounts ranging from about 0.1% to 2% by weight of the composition.

Skin active agents other than α-hydroxy carboxylic acids may also be included in compositions of the present invention. These actives may include sunscreens, tanning agents, anti-acne agents and adjunct anti-wrinkle inhibitors. Among the latter category are ceramides which are N-acylated sphingosine bases. Especially preferred are Ceramide 1, Ceramide 2 and Ceramide 3. Identity of these materials are well-outlined in "Advances in Lipid Research," Vol. 24, pgs. 27–56, by Schurer and Elias (1991 ). Levels of ceramide may range from 0.00001 to 1% by weight.

Vitamins may also be included in the compositions of the present invention. Especially preferred is Vitamin A palmitate (retinyl palmitate) and Vitamin E linoleate (tocopheryl linoleate). Other esters of Vitamins A and E may also be utilized. Combinations of tocopheryl (Vitamin E) and ascorbyl palmitate (Vitamin C) is available commercially as Oxynex K ®.

The following examples will more fully illustrate selected embodiments of this invention. All parts, percentages and proportions referred to herein and in the appended claims are by weight unless otherwise indicated.

EXAMPLE 1

Eye shadow formulas according to the present invention are outlined under Table I.

TABLE I

| Component | Weight % |
|---|---|
| Talc (Coated with Methicone) | 40–50 |
| Mica (Coated with Methicone) | 40–50 |
| Silica Beads | 3.8–5 |
| Lactic or Glycolic Acids | 0.1–5 |
| Rosmarinic Acid | 0.1–5 |
| Zinc Stearate | 0–6 |
| Nylon 12 | 2–4 |
| Boron Nitride | 5.00 |
| Methyl Paraben | 0.20 |
| Propyl Paraben | 0.10 |
| Sodium Dehydroacetate | 0.20 |
| Bismuth Oxychloride | 0–10 |
| Matricaria Extract | 0–1 |
| Rosemary Extract | 0–1 |
| Althea Extract | 0–1 |
| Sambucus Extract | 0–1 |
| Octyl palmitate | 0–5 |
| Pentaerythritol tetra (3-ethyl hexanoate) | 0–5 |
| Dimethicone | 0–5 |
| Colorants | 1–30 |

EXAMPLE 2

A series of facial foundations according to the present invention are listed under Table II.

TABLE II

| Component | Formula (Weight %) | | | | |
|---|---|---|---|---|---|
| | 1 | 2 | 3 | 4 | 5 |
| DC 3225C ® (Dimethicone/Dimethicone Copolyol) | 15.3 | 15.0 | 15.1 | 15.3 | 14.8 |
| Tioveil TG ® (40% TiO₂ in Caprylic/Capric Triglyceride) | 12.0 | 12.0 | 14.0 | 14.0 | 14.0 |
| Butylene Glycol | 7.0 | 6.0 | 6.5 | 6.0 | 6.0 |
| Cosmetic Wax 2501 (Dimethicone Copolyol) | 5.0 | 4.0 | 6.0 | 4.0 | 4.0 |
| Iron Oxides | 5.0 | 5.0 | 5.0 | 5.0 | 5.0 |
| Lactic Acid (or Na Salt) | 0.6 | 0.8 | 1.0 | — | — |
| Glycolic Acid (or Ammonium Salt) | — | — | — | 0.5 | 0.5 |
| Rosmarinic Acid (or K salt) | 0.3 | 1.0 | 0.4 | 0.1 | 0.5 |
| Aluminum Stearate Gel #22 | 5.0 | 3.0 | 4.0 | 3.0 | 3.0 |
| Zinc Stearate | 0.5 | 0.5 | 0.5 | 1.0 | 1.0 |
| DC 1403 (Dimethicone/Dimethiconol) | 1.5 | 1.0 | 1.5 | 1.0 | 1.5 |
| DC 200 (10 cst Silicone Oil) | 1.5 | 2.0 | 1.5 | 2.0 | 1.5 |
| Oxynex K (Vitamins E and C) | 0.3 | 0.3 | 0.3 | 0.3 | 0.3 |
| Squalene | 1.5 | 1.5 | 1.5 | 1.5 | 1.5 |
| Isostearyl Palmitate | 1.5 | 1.5 | 1.5 | 1.5 | 1.5 |
| Methyl Paraben | 0.2 | 0.2 | 0.2 | 0.2 | 0.2 |
| Propyl Paraben | 0.1 | 0.1 | 0.1 | 0.1 | 0.1 |
| Lecithin | 0.1 | 0.1 | 0.1 | 0.1 | 0.1 |
| Disodium EDTA | 0.1 | 0.1 | 0.1 | 0.1 | 0.1 |
| Potassium Biphosphates | 0.1 | 0.1 | 0.1 | 0.1 | 0.1 |
| Sodium Hyaluronate | 0.1 | 0.1 | 0.1 | 0.1 | 0.1 |
| Ceramides 1, 2 and 3 | 0.1 | 0.5 | 0.1 | 0.5 | 0.1 |
| α-Hydroxy Caprylic Acid | 0.1 | 0.5 | 0.1 | 0.5 | 0.1 |
| Water | qs | qs | qs | qs | qs |

EXAMPLE 3

A nonionic make-up mousse, according to the present invention, is outlined under Table III.

TABLE III

| Component | Weight % |
|---|---|
| Phase A: | |
| Isodecyl Oleate | 4.0 |
| Glycerol Dilaurate | 2.0 |
| Glycerol Stearate | 2.0 |
| Octyl Dimethyl PABA | 2.0 |
| Cetearyl Alcohol | 0.5 |
| Laureth-23 | 0.5 |
| Phase B: | |
| Water | 48.5 |
| Pigment Blend* | 12.0 |
| Hydroxy Methyl Cellulose | 3.0 |
| Propylene Glycol | 2.0 |
| Ammonium Glycolate | 1.0 |
| Rosmarinic Acid | 1.0 |
| Phase C: | |
| Ethyl Alcohol | 20.0 |
| Germaben II ® | 1.0 |
| *Pigment Blend | |
| Titanium Dioxide | 82.5 |
| Yellow Iron Oxide | 14.0 |
| Red Iron Oxide | 3.0 |
| Brown Iron Oxide | 0.5 |

EXAMPLE 4

A fast drying waterproof mascara according to the present invention is outlined under Table IV.

TABLE IV

| Components | Weight % |
|---|---|
| Phase A: | |
| Shell Sol 71(Petroleum Distillate) | 40.6 |
| Quaternium-18 Hectorite (in Petroleum Distillate and Propylene Carbonate) | 15.0 |
| Phase B: | |
| Cosmetic Black J (Iron Oxide) | 10.0 |
| Talc | 1.0 |
| Phase C: | |
| α-Hydroxy Caprylic Acid | 3.0 |

TABLE IV-continued

| Components | Weight % |
|---|---|
| Rosmarrinic Acid | 1.0 |
| Staramidopropyl Cetearyl Dimonium Tosylate | 2.0 |
| Isostearol Neopentanoate | 2.0 |
| Beeswax | 8.0 |
| Ozokerite | 8.0 |
| Trihydroxystearin | 3.0 |
| PVP/Eicosene Copolymer | 6.0 |
| Methyl Paraben | 0.1 |
| Butyl Paraben | 0.1 |
| Sorbic Acid | 0.2 |

EXAMPLE 5

A liquid eyeliner according to the present invention is outlined under Table V.

TABLE V

| Components | Weight % |
|---|---|
| Water | 80.8 |
| Sodium Lactate | 2.0 |
| Rosmarrinic Acid | 1.0 |
| Sodium Carboxymethyl Cellulose | 1.5 |
| Hectorite | 0.5 |
| Propylene Glycol | 5.0 |
| Triethanolamine-Shellac (25%) | 5.0 |
| Iron Oxide | 4.0 |
| Methyl Paraben | 0.1 |
| Germall II ® | 0.1 |

EXAMPLE 6

A blush in stick form according to the present invention is outlined under Table TABLE VI.

TABLE VI

| Components | Weight % |
|---|---|
| Phase A: | |
| Ammonium Lactate | 1.0 |
| Ammonium Rosmarrinate | 1.0 |
| $C_{18}$—$C_{36}$ Acid Triglyceride | 8.0 |
| $C_{18}$—$C_{36}$ Acid Glycol Ester | 8.0 |
| Paraffin 143/148 | 2.0 |
| Cyclomethicone | 48.8 |
| $C_{12}$—$C_{15}$ Alcohol Lactate | 8.0 |
| Tenox 4 ® (Corn Oil, BHA and BHT) | 0.1 |
| Stearyl Alcohol | 2.0 |
| Phase B: | |
| Bismuth Oxychloride | 10.4 |
| Talc | 5.0 |
| Mica | 5.5 |
| Red Iron Oxide | 0.1 |
| Methyl Paraben | 0.1 |

EXAMPLE 7

A lipstick according to the present invention is outlined under Table VII.

TABLE VII

| Components | Weight % |
|---|---|
| Polyglycerol-3 Diisostearate | 40.9 |
| Mineral Oil | 10.0 |
| Candelilla Wax | 7.0 |
| Carnauba Wax | 5.0 |
| Lanolin | 5.0 |
| Isopropyl Lanolate | 5.0 |
| PEG 20 Sorbitan Beeswax | 5.0 |
| Isopropyl Myristate | 7.0 |
| Pigments, Lakes & Dyes | 4.1 |
| Titanium Dioxide | 3.0 |
| Paraffin Wax | 2.0 |
| Beeswax | 2.0 |

TABLE VII-continued

| Components | Weight % |
|---|---|
| Potassium Lactate | 2.0 |
| Potassium Rosmarrinate | 2.0 |

EXAMPLE 8

A pair of cosmetic compositions were evaluated for stinging and/or burning potential when an α-hydroxy carboxylic acid, such as lactic acid, was applied to the face. Table III outlines the formulas utilized in the clinical test.

TABLE VIII

| | FORMULA (WEIGHT %) | |
|---|---|---|
| COMPONENT | 1 | 2 |
| Lactic Acid | 10.0 | 10.0 |
| Rosmarrinic Acid* | — | 5.0 |
| Water | qs | qs |

*As sage extract

Ten panelists, previously screened as lactic acid "stingers" were recruited for the study. Both males and females were enrolled, ranging in age from 25 to 55. The study took place over a two day period. Panelists were instructed to remove make-up on their faces by washing with soap and water at least one hour prior to test time. At the test time, each panelist washed the cheek area with Cetaphil ®, a gentle cleanser. Then faces were padded dry with a paper towel. After a five minute rest period, 0.05 cc of test product was applied to a weighing boat via tuberculin syringe (without a needle). The product was rubbed into the test site for 20 seconds using a finger cot.

Each test product was generously applied, to the nasolabial folds and cheeks of eight panelists. The subjects were questioned about stinging responses at 10 seconds, 2.5 minutes, 5.0 minutes and 8.0 minutes after product application. The following scale was used:

0 = no stinging
1 = light discomfort
2 = moderate discomfort
3 = severe stinging/burning Two products were evaluated on a panelist, one on each side of the face. A randomization schedule was employed.

Some substances may cause slight to severe stinging immediately after application with disappearance of the sensation within 5 to 30 seconds. Delayed stinging generally is not preceded by a transient phase and usually becomes evident within a minute or two. The delayed stinging score for an individual is the mean of the three readings at 2.5, 5.0 and 8.0 minutes. Substances with average scores falling between 0.4 and 1.0 have a slight stinging potential. The range 1.1 to 2.0 signifies moderate stinging, and 2.1 to 3.0 denotes severe stinging.

The Overall Average stinging response for the 10.0% lactic acid Formula 1 was 1.565. An identical amount of lactic acid in combination with 5% rosmarrinic acid (as sage extract) provided an Overall Average stinging response of 0.432. These results demonstrate that the combination of rosmarrinic acid with lactic acid substantially reduces the level of stinging.

The foregoing examples illustrate only selected embodiments of the present invention and should be considered nonlimiting examples with variations and modifications thereof all being within the spirit and purview of this invention.

What is claimed is:

1. A cosmetic facial foundation composition comprising:
   (i) from about 0.01 to about 10% by weight of a $C_2$–$C_{28}$ α-hydroxy carboxylate compound selected from the group consisting of glycolic acid, lactic acid and their salts and combinations thereof;
   (ii) from about 0.05 to about 5% by weight of rosmarrinic acid or salt thereof; and
   (iii) from about 1 to about 99.9% by weight of a pharmaceutically acceptable carrier.

2. A cosmetic composition according to claim 1, further comprising a volatile or non-volatile silicone oil in an amount ranging from about 1 to about 70% by weight of a composition.

3. A cosmetic composition according to claim 1, further comprising from about 0.1 to about 20% by weight of titanium dioxide.

4. A cosmetic composition according to claim 1, further comprising from about 0.1 to about 20% by weight of iron oxides.

5. A cosmetic composition according to claim 1, further comprising from about 0.00001 to about 1% by weight of a ceramide.

6. A cosmetic composition according to claim 1 which is an oil and water emulsion.

7. A cosmetic composition according to claim 1, further comprising from about 1 to about 30% of a cyclomethicone-dimethicone copolyol silicone fluid having a viscosity of 600–2000 cps at 25° C.

8. A cosmetic composition according to claim 7, further comprising from about 0.1 to about 5% of a dimethicone-dimethiconol silicone fluid having a viscosity of about 4000 cs at 25° C.

* * * * *